United States Patent
Price

(10) Patent No.: US 8,656,955 B2
(45) Date of Patent: Feb. 25, 2014

(54) ROTARY COLUMN SELECTOR VALVE

(75) Inventor: Glenn Price, Martinez, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 319 days.

(21) Appl. No.: 13/110,614

(22) Filed: May 18, 2011

(65) Prior Publication Data

US 2012/0125440 A1    May 24, 2012

Related U.S. Application Data

(60) Provisional application No. 61/346,752, filed on May 20, 2010.

(51) Int. Cl.
*F16K 11/074* (2006.01)

(52) U.S. Cl.
USPC .................... 137/625.46; 137/625.15

(58) Field of Classification Search
USPC .............. 137/625.46, 625.11, 625.15, 625.13
See application file for complete search history.

(56) References Cited

U.S. PATENT DOCUMENTS

| | | | |
|---|---|---|---|
| 3,451,428 A * | 6/1969 | Pruett | 137/625.46 |
| 3,796,232 A | 3/1974 | Dalton | |
| 3,868,970 A | 3/1975 | Ayers et al. | |
| 4,174,925 A | 11/1979 | Pfenning et al. | |
| 5,803,117 A | 9/1998 | Olsen et al. | |
| 6,453,946 B2 | 9/2002 | Nichols et al. | |
| 6,672,336 B2 | 1/2004 | Nichols | |
| 7,377,291 B2 | 5/2008 | Moon et al. | |
| 7,503,203 B2 | 3/2009 | Gamache et al. | |
| 2004/0112444 A1 | 6/2004 | Hofmann | |
| 2009/0107332 A1 | 4/2009 | Wagner | |
| 2010/0032603 A1 | 2/2010 | Wilen | |
| 2010/0058841 A1 | 3/2010 | Wilen | |

FOREIGN PATENT DOCUMENTS

WO    WO 2008/103097    *    8/2008    ............. G01N 30/20

OTHER PUBLICATIONS

User's Manual, AKTA avant 25; Chromatography Systems, GE Healthcare (Aug. 2009).
International Search Report mailed Sep. 22, 2011 for PCT Application No. PCT/US2011/037380.

* cited by examiner

*Primary Examiner* — John Rivell
*Assistant Examiner* — Michael R Reid
(74) *Attorney, Agent, or Firm* — Kilpatrick Townsend & Stockton LLP

(57) ABSTRACT

A rotary valve is designed to include a stator with multiple pairs of ports for connection to flow-through components and a rotor with elongated recesses that form flow channels with minimal dead volume and that permit a reversal of flow direction through any component by rotation of the valve through a very small angle.

18 Claims, 3 Drawing Sheets

ROTARY COLUMN SELECTOR VALVE

CROSS-REFERENCE TO RELATED APPLICATION

This application claims the benefit of U.S. Provisional Patent Application No. 61/346,752, filed May 20, 2010, the contents of which are incorporated herein by reference.

BACKGROUND OF THE INVENTION

Rotary valves are useful in analytical laboratories and instrumentation for directing fluid flows to system components such as columns, loops, filters, detectors, and the like, and for switching between different components as well as different fluid sources. Rotary valves can thus be used to select and switch between components for such purposes as sample injection, sample stream selection, fluid redirection, fraction collection, solvent or buffer selection, and selections between different chromatography columns. The typical rotary valve has a stator and a rotor, with internal channels, usually in the form of grooves (elongated recesses) in the surface of either the stator or the rotor, most often the rotor, that bridge selected pairs of ports in the valve depending on the position of the rotor. In the typical rotary valve supplying a flow-through system component such as an analytical column, an internal channel in the valve will form a bridge between an inlet port on the valve and an inlet port to the flow-through component, while another internal channel in the valve will form a bridge between an outlet port from the same flow-through component and an outlet port on the valve. The internal channels typically contain a certain amount of dead volume, defined herein as a region of an internal channel through which fluid does not flow but is instead stagnant, while fluid is flowing elsewhere through the valve. A valve with dead volume must be cleaned periodically, and even with cleaning, the dead volume poses a risk of contamination of one fluid or sample with another when the valve position is switched. Aside from dead volume, the distance that the fluids travel through the internal channels can affect the efficiency of the component to which the fluids are directed. When the valve is utilized on chromatographic systems, for example, the additional travel distance through the internal channels of the valve can result in band broadening, reducing the precision with which solutes are detected and quantified. Certain rotary valves are also designed to provide the user with a choice between forward and reverse flow directions through a flow-through component. This complicates the valve design and in certain cases requires rotation of the valve by 180 degrees, raising the possibility of user error when the valve is rotated too far or not far enough, and the possibility of contamination when the valve must be rotated past one or more positions to reach the desired position.

SUMMARY OF THE INVENTION

The present invention resides in a rotary valve that contains minimal dead volume and that permits a reversal of flow direction through any component by rotation of the valve through a very small angle. These and other features, objects, and advantages of the invention will be apparent from the attached drawings and the description that follows.

DETAILED DESCRIPTION OF THE INVENTION AND PREFERRED EMBODIMENTS

Figure 1:
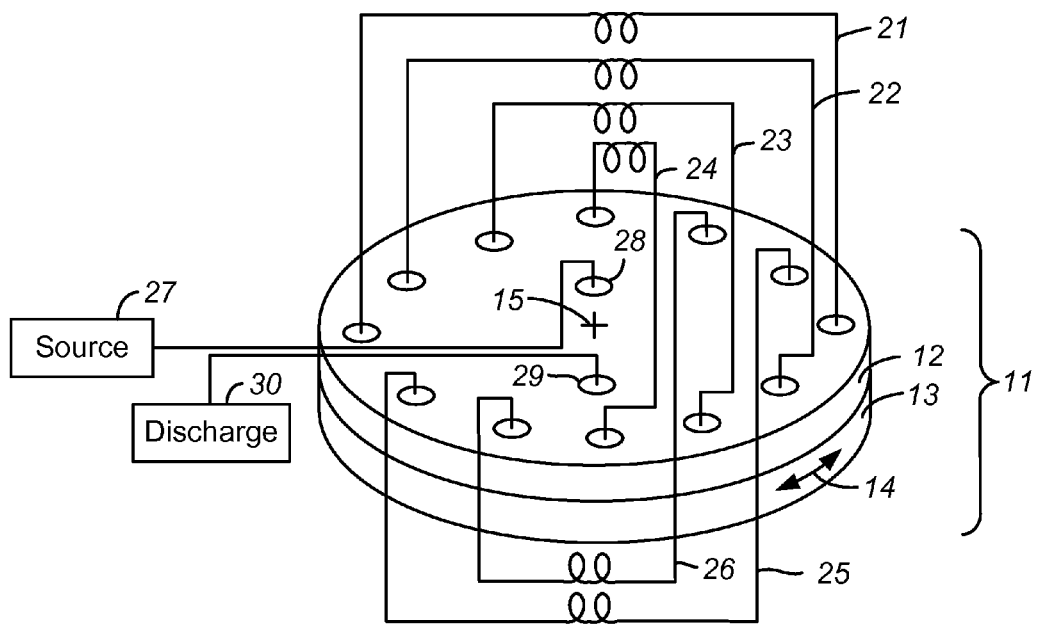
FIG. 1 is a perspective view of a rotary valve within the scope of the present invention.

The term "component," as noted above, is used herein to denote units that the rotary valve supplies liquid to or receives liquid from. Many such units are flow-through units. Examples of such "components" are columns, loops, filters, and detectors. The term "component port" is used herein to denote a port in the rotary valve to which a component is connected, in many cases through connective tubing. Component ports serve to either supply fluid to, or receive fluid from, components, and the typical component will be connected to two component ports, one for supplying fluid to the component and the other to receive fluid leaving the component.

The term "valve inlet port" is used herein to denote a port in the rotary valve that is designated to receive fluid from a source of supply of the fluid external to the valve, and through which the fluid enters an internal channel of the valve for conveyance to a component port. Likewise, the term "valve outlet port" is used herein to denote a port designated to discharge fluid from the interior of the valve, and in particular from an internal channel of the valve, to a receptacle outside the valve, which receptacle can be a further unit such as a detector, a collection vessel, or waste.

The term "arc" in reference to a circle denotes a segment of a circle that extends less than the full circumference of the circle.

The term "opposing each other across said axis" when used herein to describe the position relationship between two ports indicates that a straight line connecting the two ports passes through the axis with the axis lying between the two ports.

Among the characteristic features of the rotary valve of the present invention is a rotor with two elongate recesses or grooves in the surface of the rotor facing the stator, each groove shaped to form an arc of a circle whose center is at the axis of the valve, and two arms extending outward from the arc (i.e., away from the axis). The two recesses are entirely separate; there is no means for fluid to flow from one to the other. The two arcs face each other across the axis. The stator contains the component ports arranged in pairs directly opposing each other across the common axis of the stator and rotor. The paired component ports are laid out in arcs flanking the axis, with the axis at the centers of each of these arcs. The arcs formed by the component ports are larger in radius than, and thus reside outside, the arcs in the rotor recesses. The outer termini of the arms that are part of the recesses in the rotor are aligned with the arcs foamed by the component ports in the stator so that as the rotor rotates, each arm terminus passes from alignment with one component port to alignment with the next component port of the same arc, and thus all component ports of that arc, in succession.

Further characteristic features include a single valve inlet port and a single valve outlet port in the stator, each of these ports located at a radial distance from the axis that is equal to the radius of one of the arc portions of the recess. Thus, as the rotor rotates, the arc portion of one recess passes over the valve inlet port and the arc portion of the other recess passes over the valve outlet port, both ports remaining aligned with the respective arc portions, each port thus maintaining fluid communication with one recess. Preferably, neither the stator nor the rotor contains any port or recess that either is at the axis or traverses the axis.

Dead volume in any single recess is limited to the portion of the arc that is not in use and the arm that is not in use, and the length of each recess through which fluid flows during active use of the recess is limited to one of the two arms and a portion of the arc. Furthermore, while the length of each recess through which fluid flows varies with the position of the valve, the range of variation is only the length of the arc in each recess, a relatively small distance. Still further, the lengths of the two recesses are either the same or differ by a minimal amount, and each recess can therefore accommodate fluid flow in either direction with no change in the fluid path. Still further, the two recesses are positioned such that the termini of the arms of one recess are sufficiently close to the termini of the arms of the second recess that only a small angular rotation will result in reversing the flow direction through any single component to which the valve is connected.

The figures supplied herewith depict examples of rotary valves within the scope of this invention.

FIG. 1 is a perspective view of one example of a rotary valve 11 within the scope of this invention. The valve body is formed from two disks, with the stator 12 as the upper disk and the rotor 13 as the lower disk, whose rotation is indicated by the arrow 14. The two disks share a common axis 15 which is the axis about which the rotor 13 rotates. The valve in this example accommodates six components 21, 22, 23, 24, 25, 26, each represented by a loop and each connected to two ports in the valve. Fluid for feeding to the loops is supplied to the valve from a supply source 27 through a valve inlet port 28 and fluid leaving the loops is discharged from the valve through a valve outlet port 29 to a discharge receptacle 30. Channels joining the valve inlet and outlet ports are in the rotor. These channels and the various ports in the stator are more clearly visible in FIGS. 2 and 3.

Figure 2:
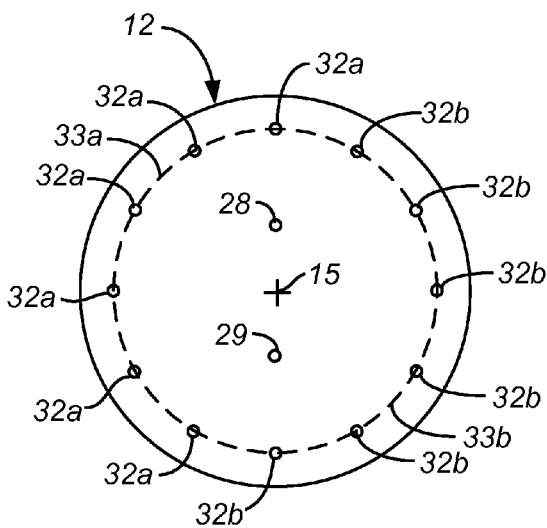
FIG. 2 is a plan view of the stator of the rotary valve of FIG. 1.

FIG. 2 is a plan view of the stator 12. The component ports 32a, 32b are open to both sides of the stator, extending through the full thickness of the stator disk. The component ports are in pairs, with the two members of each pair directly opposing each other across the axis 15. Designating one port of each pair an inlet port 32a and the other an outlet port 32b for purposes of illustration, the inlet ports 32a are arranged along an arc 33a of a circle and the outlet ports 32b are also arranged along an arc 33b of a circle, the arcs being concentric and their centers coinciding with the axis 15. In the particular embodiment shown in FIGS. 1, 2, and 3, the radii of the two arcs 33a, 33b are equal in length, the two arcs being arcs of the same circle. Alternatively, the two arcs can be of unequal radii, as illustrated in subsequent Figures and explained below. A further feature of the embodiment of FIG. 2 is the equal spacing, i.e., equal angular displacement of all of the component ports along each arc and around the entire circumference of the stator. Alternative arrangements with unequal spacings of the ports within each arc, or with wider angular gaps between the group of inlet ports and the group of outlet ports, or both, are likewise within the scope of the invention. The valve inlet port 28 and the valve outlet port 29 are both inside the arcs formed by the component ports and thereby closer to the axis 15. As shown, they are equidistant from the axis, although this too can vary, as is also shown in subsequent Figures.

Figure 3:
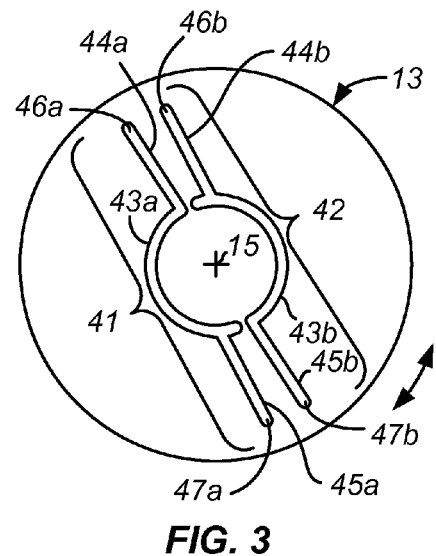
FIG. 3 is a plan view of the rotor of the rotary valve of FIG. 1.

FIG. 3 is a plan view of the rotor 13. The recesses 41, 42 that connect the various component ports to the valve inlet and outlet ports in the stator are not openings that pass through the thickness of the rotor, but instead grooves in the surface of the rotor that faces the stator, forming closed channels with the stator surface. Each recess includes an arc 43a, 43b, the two arcs being concentric, with the centers of each arc coinciding with the axis 15. At or near the two ends of each arc are arms 44a, 45a, 44b, 45b extending from the arc outward. The outer extremities of the arms are the termini 46a, 47a, 46b, 47b of the recesses, each terminus being the same distance from the axis 15 as the component ports 32a, 32b in the stator. Thus, as the rotor rotates, the termini 46a, 47a, 46b, 47b align with the component ports 32a, 32b in succession. Likewise, the arc portions 43a, 43b of the recesses have radii that are equal to the distances between the valve inlet and outlet ports 28, 29 in the stator, and thus as the rotor rotates, the valve inlet and outlet ports 28, 29 remain aligned with these arc portions 43a, 43b. In this embodiment, the two arc portions 43a, 43b have equal radii and are arcs of the same circle. Alternatively, the two arcs can be of different radii, as illustrated in subsequent Figures and explained below. Also in this embodiment, the arms 44a, 45a, 44b, 45b are of approximately equal length and the termini 46a, 47a, 46b, 47b are all equidistant from the axis. Alternative designs in which the termini 46a, 47a, 46b, 47b are of different lengths, will also function and are within the scope of this invention. This variation is likewise illustrated in subsequent Figures and discussed below.

Figure 4:
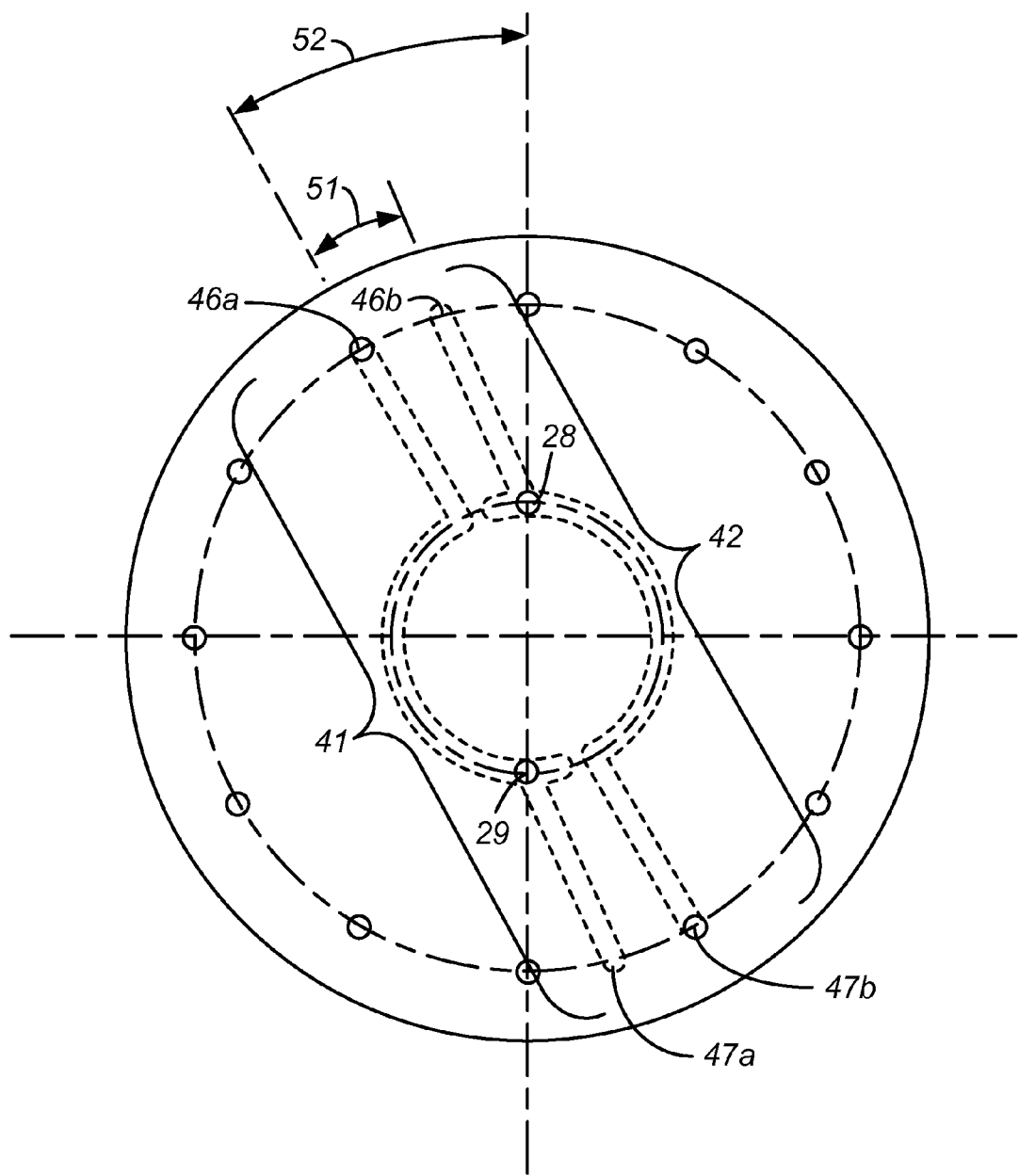
FIG. 4 is a plan view of the combined stator and rotor of the rotary valve of FIG. 1.

FIG. 4 shows the stator and rotor joined, with the rotor beneath the stator, and the recesses 41, 42 shown in dashed lines. The recesses 41, 42 are arranged such that the spacings between the termini 46a, 47a, 46b, 47b are not equal to those between the component ports, and at all positions of the valve at most one terminus from each recess is aligned with a component port. Thus, at each position in which the valve opens into a component, one recess connects the valve inlet port 28 with one component port, and the other recess connects the valve's outlet port 29 with one other component port, the two component ports forming the pair that supplies fluid to and receives fluid from a single component. In preferred embodiments, such as that shown, the angular spacing 51 between the terminus 46a of one recess and the adjacent terminus 46b of the other recess is less than, in this case approximately half, the angular spacing 52 between adjacent component ports. By rotating the rotor through an angle equal to the angular spacing 52 between adjacent component ports, fluid flow through the valve is switched from one component to the next; by rotating the rotor through the smaller angular spacing 51 between adjacent termini of the recesses in the rotor, the direction of fluid flow through a single component can be reversed.

Figure 5:
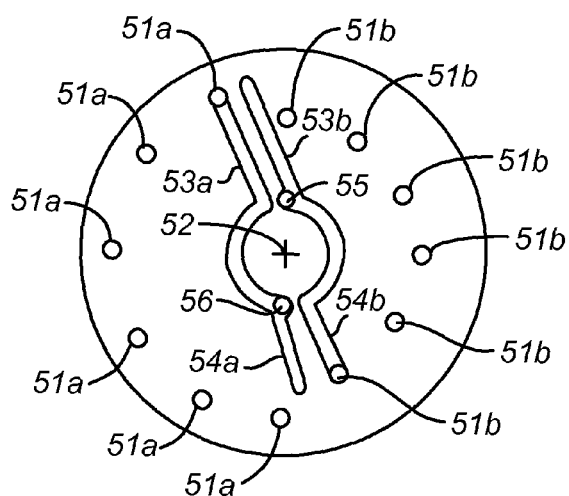
FIG. 5 is a plan view of combined stator and rotor of the rotary valve of a second rotary valve within the scope of the present invention.
Figure 6:
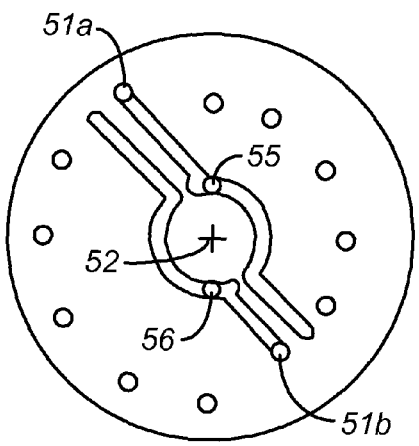
FIG. 6 is a plan view of combined stator and rotor of the rotary valve of FIG. 5 in a reverse-flow position.

A variation on the rotary valve of FIGS. 1 through 4 is shown in FIGS. 5 and 6. These figures depict a stator and rotor joined to each other in a view analogous to that of FIG. 4, except that for clarity, all ports and recesses are shown in solid lines. In FIGS. 5 and 6, the two sets of component ports 51a, 51b form arcs that are not of equal radii although both are centered on the valve axis 52. Correspondingly, each recess has a long arm 53a, 53b and a short arm 54a, 54b. The lengths of these arms are such that in the valve position shown in FIG.

5, the terminus of the long arm (for example 53a) of one recess will align with one component port 51a and the terminus of the short arm (for example 54b) will align with the opposing component port 51b. The flow paths are analogous to those of the rotary valve of FIGS. 1 through 4, with fluid being supplied to the valve through the valve inlet port 55 and being drawn from the valve through the valve outlet port 56. Reversal of the flow direction through the same component is achieved by rotating the rotor to the position shown in FIG. 6, where the same component port 51a that communicated with the valve outlet port 56 in the FIG. 5 position now communicates with the valve inlet port 55, while the opposing component port 51b that communicated with the valve inlet port 55 in the FIG. 5 position now communicates with the valve outlet port 56.

Figure 7:
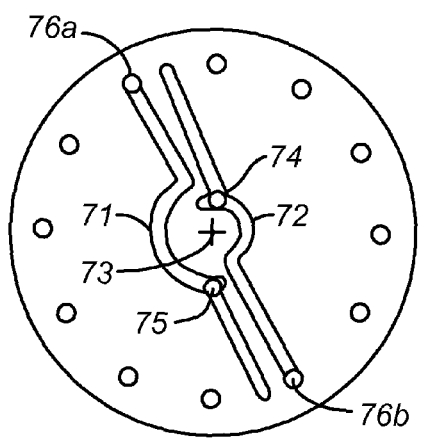
FIG. 7 is a plan view of combined stator and rotor of the rotary valve of a third rotary valve within the scope of the present invention.
Figure 8:
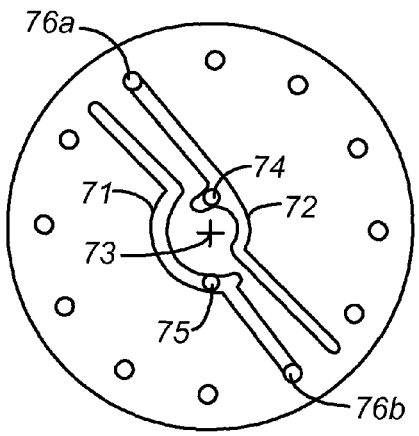
FIG. 8 is a plan view of combined stator and rotor of the rotary valve of FIG. 7 in a reverse-flow position.

A second variation is shown in FIGS. 7 and 8. These figures likewise depict a stator and rotor joined to each other in a view analogous to those of FIGS. 5 and 6, with all ports and recesses shown in solid lines. In FIGS. 7 and 8, the arc portions 71, 72 of the two recesses in the rotor are not arcs of the same circle but instead of circles of different radii, although both are still centered on the axis 73. Correspondingly, the valve inlet port 74 is not the same distance from the axis as the valve outlet port 75, the valve inlet port 74 being aligned with the arc 72 of one recess and the valve outlet port 75 being aligned with the arc 71 of the other recess. The flow paths are again analogous however to those of the rotary valves of the preceding Figures, with fluid being supplied to the valve through the valve inlet port 74 and being drawn from the valve through the valve outlet port 75. Reversal of the flow direction through the same component is achieved by rotating the rotor from the position shown in FIG. 7 to the position shown in FIG. 8, where the same component port 76a that communicated with the valve outlet port 75 in the FIG. 7 position now communicates with the valve inlet port 74, while the opposing component port 76b that communicated with the valve inlet port 74 in the FIG. 7 position now communicates with the valve outlet port 75.

In the embodiments shown in the various Figures, six pairs of component ports are included in each rotary valve. The number is not critical to the invention and can vary. Preferably, the valve will contain from two to ten pairs, and most preferably from four to eight pairs. The angular spacings between adjacent ports will vary correspondingly. In the six-pair arrangement shown, the angular spacing to switch from one component to the next is 30 degrees, while the angular spacing to switch from forward to reverse flow (or vice versa) in the same component is 15 degrees. The relative radii of the arcs can also vary. In preferred embodiments, the radii of the arc portions of the recesses in the rotor are one-quarter to three-quarters the radii of the arcs in which the component ports reside. The lengths of the arcs can vary as well, depending on how many positions that valve has and how far apart the adjacent ports are, or that full range of rotation of the valve. In preferred embodiments, each arc is less than half the circumference of the circle defined by the arc.

Other features of the valve construction are conventional and well known in the art. The stator and rotor are generally pressed together to create a surface seal that does not allow the passage of fluids between the contacting surfaces other than through the channels formed by the recesses. Preferred surfaces are also resistant to wear. Ceramics and ceramic-polymer combinations are among those known in the art for this purpose.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A rotary valve comprising a stator and a rotor mounted to said stator for rotation about an axis,
    said stator having (i) a plurality of pairs of component ports, each pair consisting of a first component port and a second component port opposing each other across said axis, said first component ports collectively arranged in an arc of a first circle centered on said axis and said second component ports collectively arranged in an arc of a second circle centered on said axis, and (ii) a valve inlet port and a valve outlet port opposing each other across said axis, said valve inlet and valve outlet ports both positioned inside said first and second circles;
    said rotor having first and second elongate recesses having no fluid communication with each other, said first recess comprising an arc of a third circle that is centered on said axis and is equidistant from said axis with said valve inlet port, said second recess comprising an arc of a fourth circle that is centered on said axis and is equidistant from said axis with said valve outlet port, each of said first and second recesses further comprising a first arm extending from said arc to a first terminus at said first circle of component ports in said stator and a second arm extending from said arc to a second terminus at said second circle of component ports in said stator,
    wherein said first termini are separated along said first circle of component ports by an angular spacing that is less than the angular spacing between adjacent first component ports of said stator, and said second termini are separated along said second circle of component ports by an angular spacing that is less than the angular spacing between adjacent second component ports of said stator.

2. The rotary valve of claim 1 wherein said arc of said first circle is less than half the circumference of said first circle, and said arc of said second circle is less than half the circumference of said second circle.

3. The rotary valve of claim 1 wherein said arc of said third circle is less than half the circumference of said third circle, and said arc of said fourth circle is less than half the circumference of said fourth circle.

4. The rotary valve of claim 1 wherein said first circle and said second circle coincide such that all of said component ports are arranged in a common circle.

5. The rotary valve of claim 1 wherein said third circle and said fourth circle coincide such that said arc of said third circle and said arc of said fourth circle are arcs of a common circle.

6. The rotary valve of claim 1 wherein said plurality of pairs of component ports consists of from two pairs to ten pairs.

7. The rotary valve of claim 1 wherein said plurality of pairs of component ports consists of from four pairs to eight pairs.

8. The rotary valve of claim 1 wherein said first component ports of said stator are spaced apart by equal annular spacings, and said angular spacing of said first termini is approximately one-half of said angular spacing between said first component ports.

9. The rotary valve of claim 1 wherein no ports or recesses are either positioned at or traverse said axis.

10. A method for passing fluid through a flow-through component connected to the rotary valve of claim 1 in first and second directions in succession said second direction being the reverse of said first direction, said method comprising:
  (a) with said flow-through component having first and second ends connected to first and second component ports, respectively, of a selected pair of component ports in said rotary valve, and with said rotary valve in a first rotary position whereby a first flow path is formed from said valve inlet port through said first elongate recess to said first component port, and a second flow path is formed from said second component port through said second elongate recess to said valve outlet port, feeding a first fluid into said rotary valve through said valve inlet port and discharging effluent from said first fluid from said rotary valve through said valve outlet port, thereby causing said first fluid to pass through said flow-through component in a forward direction,
  (b) rotating said rotor of said rotary valve to a second rotary position wherein a third flow path is formed from said valve inlet port through said first elongate recess to said second component port, and a fourth flow path is formed from said first component port through said second elongate recess to said valve outlet port, and
  (c) feeding a second fluid into said rotary valve through said valve inlet port and discharging effluent from said second fluid from said rotary valve through said valve outlet port, thereby causing said second fluid to pass through said flow-through component in a reverse direction.

11. The method of claim 10 wherein said arc of said first circle is less than half the circumference of said first circle, and said arc of said second circle is less than half the circumference of said second circle.

12. The method of claim 10 wherein said arc of said third circle is less than half the circumference of said third circle, and said arc of said fourth circle is less than half the circumference of said fourth circle.

13. The method of claim 10 wherein said first circle and said second circle coincide such that all of said component ports are arranged in a common circle.

14. The method of claim 10 wherein said third circle and said fourth circle coincide such that said arc of said third circle and said arc of said fourth circle are arcs of a common circle.

15. The method of claim 10 wherein said plurality of pairs of component ports consists of from two pairs to ten pairs.

16. The method of claim 10 wherein said plurality of pairs of component ports consists of from four pairs to eight pairs.

17. The method of claim 10 wherein said first component ports of said stator are spaced apart by equal annular spacings, and said angular spacing of said first termini is approximately one-half of said angular spacing between said first component ports.

18. The method of claim 10 wherein no ports or recesses are either positioned at or traverse said axis.

* * * * *